Figure 1:
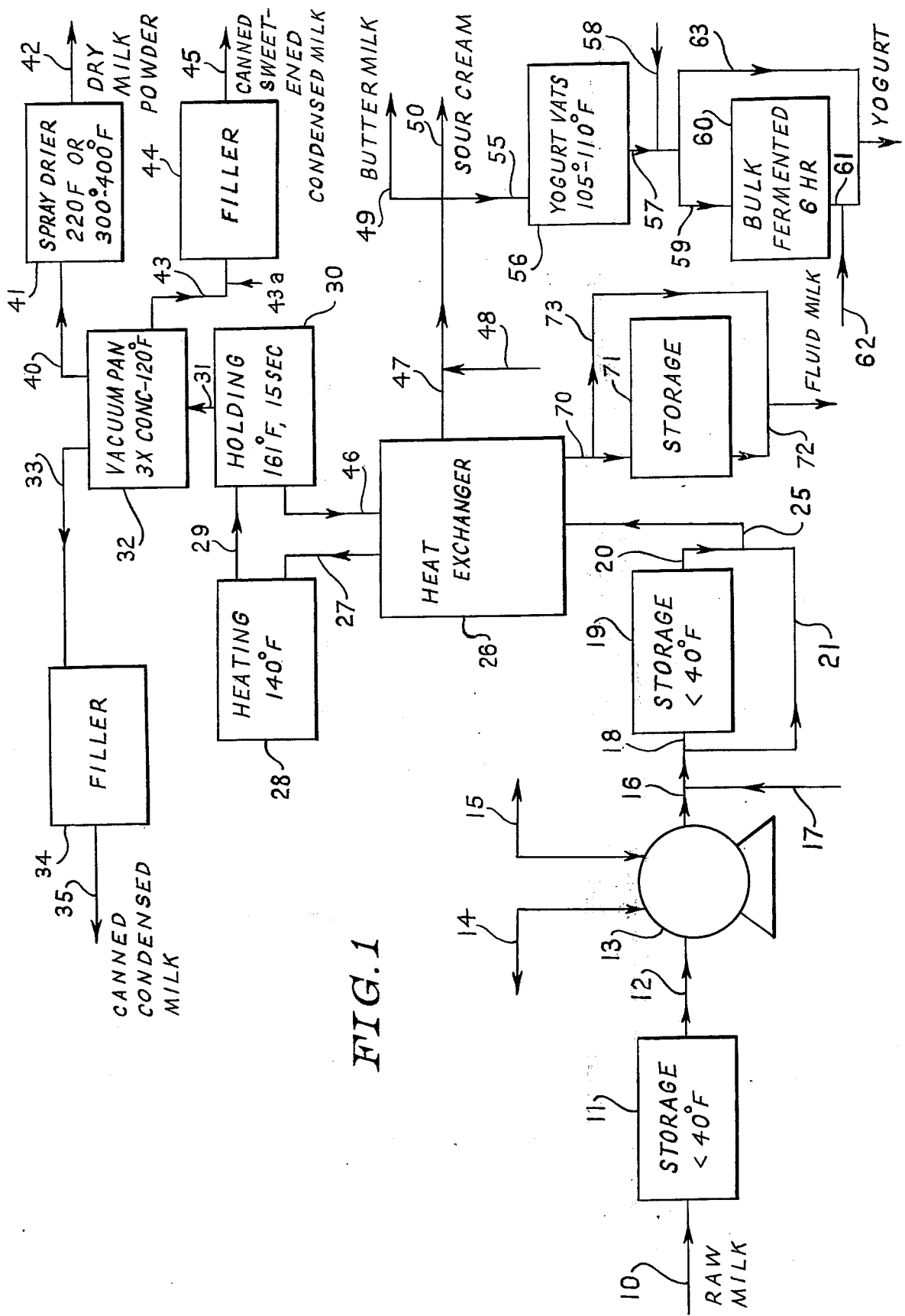

United States Patent [19]

Crisan et al.

[11] 4,007,283
[45] Feb. 8, 1977

[54] PRODUCTION AND UTILIZATION OF LACTASE

[75] Inventors: Eli V. Crisan, Davis; Steven G. Sorensen, Palo Alto, both of Calif.

[73] Assignee: The Regents of the University of California, Berkeley, Calif.

[22] Filed: Oct. 28, 1975

[21] Appl. No.: 626,133

[52] U.S. Cl. .............................. 426/34; 195/31 R; 195/62; 195/66 R; 195/111; 426/42
[51] Int. Cl.² .................. C12D 13/10; A23C 9/12; A23C 21/00
[58] Field of Search ............. 195/81, 66 R, 65, 62, 195/31 R, 111, 82; 426/34, 43, 42

[56] References Cited
UNITED STATES PATENTS

| | | | |
|---|---|---|---|
| 3,592,739 | 7/1971 | Sternberg | 195/66 R |
| 3,816,259 | 6/1974 | Collinge et al. | 195/66 R |

OTHER PUBLICATIONS

Sivers et al., "B–Galactosidase Activity of Microscopic Fungi," Chemical Abstracts, vol. 79, p. 212, abs. No. 102573n, (1973).

Primary Examiner—A. Louis Monacell
Assistant Examiner—Thomas G. Wiseman
Attorney, Agent, or Firm—Edward B. Gregg

[57] ABSTRACT

Thermostable lactase produced by growth of thermophilic fungi, harvesting resulting mycelium, separating lactase from mycelium by radical rupture of cell structure or by subjecting cell structure to milder treatment which does not separate lactase from the structure, and separating cell debris. Resulting lactase has high degree of activity and is thermostable such that it can be used at relatively high temperatures, e.g. 60° C., and at acid pH to catalyze hydrolysis of lactose to glucose and galactose.

21 Claims, 6 Drawing Figures

PRODUCTION AND UTILIZATION OF LACTASE

This invention relates to the production and utilization of beta-D-galactoside galactohydrolase having the numerical designation E.C. 3.2.1.2.3 (E.C. referring to Enzyme Commission). For convenience, the term "lactase" will be used hereinafter to designate this enzyme.

Lactose is an abundant disaccharide which is present in milk and in certain dairy products such as yogurt and whey. However, its nutritional value is limited because of the fact that a large proportion of the human population lacks the intestinal enzyme lactase. As a result, the lactose content of milk and other dairy products is not utilized or is only partially utilized by many persons.

Lactase extracted from natural sources may be used to hydrolyze lactose to glucose and galactose, which are more easily assimilated. One of the best known sources of lactase is the yeast of *Kluyveromyces fragilis*. Other known sources are other yeasts, and certain bacteria and fungi. However, lactase as prepared heretofore from such sources has exhibited low activity or it is heat labile and rapidly loses its activity at elevated temperatures such as 50° to 60° C. Another problem encountered in providing sources of lactase is that some organisms do not undergo cell growth at an adequately rapid rate. Inasmuch as lactase production is proportional to cell production, yields of lactase from such sources are low.

It is an object of the present invention to improve upon the production of lactase by producing this enzyme at commercially acceptable rates and in a thermostable, highly active form which does not undergo rapid inactivation at elevated temperatures such as 50° to 60° C.

The above and other objects of the invention will be apparent from the ensuing description and the appended claims.

We have discovered that lactase having a high degree of activity and the ability to retain its activity for considerable periods of time at elevated temperatures, that is to say highly active, thermostable lactase, can be produced at acceptable rates by growing thermophilic fungi, harvesting the resulting mycelium and extracting the enzyme or an enzyme rich fraction from the harvested mycelium. We have also discovered that this lactase has a high degree of activity at acid pH.

Representative genera and species of thermophilic fungi are as follows:

Zygomycetes

*Absidia corymbifera*
*Mortierella turficola*
*M. wolfi*
*Mucor miehei*
*M. pusillus*
*Rhizomucor sp.*
*Rhizopus arrhizus*
*R. cohnii*
*R. microsporus*

Ascomycetes

*Alleschria terrestris*
*Byssochlamys verrucosa*
*Chaetomium britannicum*
*C. thermophile*
*C. thermophile var. coprophile*
*C. thermophile var. dissitum*
*C. virginicum*
*Emericella nidulans*
*Hansenula polymorpha*
*Myriococcum albomyces*
*Sphaerospora saccata*
*Talaromyces byssochlamydoides*
*T. emersonii*
*T. leycettanus*
*T. thermophilus*
*Thermoascus aurantiacus*
*T. crustaceus*
*Thielavia australiensis*
*T. sepedonium*
*T. thermophila*

Basidiomycetes

*Coprinus delicatulus*

Mycelia Sterila

*Burgoa-Papulaspora*
*Papulaspora thermophila*

Deuteromycetes

*Acremonium albamensis*
*Acrophialophora fusispora*
*Aspergillus candidus*
*A. fumigatus*
*Botrytis sp.* (= *Sphaerospora saccata*)
*Calcarisporium thermophile*
*Cephalosporium sp.* (= Alleschria terrestris)
*Cephalosporium sp.* (= Thielavia australiensis)
*Geotrichum sp. A*
*Humicola grisea var. thermoidea*
*H. insolens*
*H. lanuginosa*
*H. stellata*
*Malbranchea pulchella var. sulfurea*
*Nodulisporium cylindroconium* (Tritirachium sp. A)
*Paecilomyces crustaceus* (= Thermoascus)
*P. puntonii*
*P. variotii*
*Paecilomyces sp.* (= *Byssochlamys verrucosa*)
*Paecilomyces sp.* (= *Talaromyces byssochlamydoides*)
*Penicillium duponti* (= *Talaromyces thermophilus*)
*P. emersonii* (= Talaromyces)
*P. leycettanum* (= Talaromyces)
*P. piceum*
*P. argillaceum*
*Ptychogaster sp.* (*Sporotrichum pulverulentum*)
*Scolecobasidium sp. A* ( = *Diplorhinotrichum galloparum*)
*Sporotrichum thermophile* (= Thielavia)
*S. pulverulentum*
*Stilbella thermophila*
*Thermomyces ibadanesis*
*Torula thermophila*
*Torulopsis candida*
*Tritirachium sp. A* (= *Nodulisporium cylindroconium*)

We have achieved our best results with those thermophilic fungi which are classed as filamentous, but other thermophilic fungi may be as good.

Not every species, nor as far as we know not every genus of this category (thermophilic fungi) is capable of producing highly active thermostable lactase. Within a given species, there may be variations from one strain or variety to another, some being better than others with respect to cell yield and/or enzyme activity and/or thermal stability. Further, it may be possible, with a strain or species which does not meet these criteria in adequate degree, to induce the desired result by proper selection or manipulation of the culture medium. Thus, given a species and or given a strain or variety of thermophilic fungi of this category of organisms which does not thrive initially upon a culture medium in which lactose is the sole carbon source, it may be possible to induce such ability by growing the organism on a medium containing both lactose and another more readily assimilable carbon source such as glucose, and then transferring the organisms from one culture medium to another, the successive media having diminished proportions of glucose and larger proportions of lactose until organisms result which will grow upon a medium containing lactose as the sole source of carbon.

The choice of a species, and within a species the choice of a strain or variety, which will accomplish the desired result and will produce lactase at acceptable yield and having adequate thermal stability and activity, is a process of systematic testing and assay procedures. Once a satisfactory species and a satisfactory strain or variety of that species have been provided, it will provide a suitable continuing source of the organism for the production of lactase in yields and of qualities desired.

A considerable variety of culture media may be used. Two such media are as follows:

| Lilly and Barnett's Basal Semi-synthetic Medium (modified) | |
|---|---|
| Lactose | 9 grams |
| Asparagine | 2 g |
| $KH_2PO_4$ | 1 g |
| $MgSO_4.7 H_2O$ | 0.5 g |
| $Fe^{+++}$ | 0.2 milligrams |
| $Zn^{++}$ | 0.2 mg |
| $Mn^{++}$ | 0.1 mg |
| Biotin | 5 micrograms |
| Thiamin | 100 $\mu$g |
| Distilled water to make | 1 liter |

(Lilly, V. G. & H. L. Barnett. "Physiology of the Fungi." 464 pp. McGraw-Hill Book Co., Inc., New York.) (p. 427.)

| Sucrose Mineral Agar (Czapek-Dox Agar) (modified) | |
|---|---|
| Lactose | 10 grams |
| Asparagine | 3 g |
| $K_2HPO_4$ | 1 g |
| $MgSO_4 \cdot 7 H_2O$ | 0.5 g |
| KCl | 0.5 g |
| $FeSO_4 \cdot 7 H_2O$ | 0.1 g |
| Water to make | 1 liter |

(Stevens, R. B. (ed.) "Mycology Guidebook." 703 pp. University of Washington Press, Seattle.) (p. 683.)

Other appropriate culture media containing sufficient nutrients and an organic nitrogen source such as asparagine and to which lactose can be added as a major, if not sole, source of carbon. (Several are listed in Stevens, op. cit.) Reference may be had to R. B. Stevens, "Mycology Guidebook", University of Washington, 1974 for other suitable culture media. In commercial practice a waste product free from major amounts of carbon sources other than lactose may be used, to which lactose is added as the carbon source. Such waste products will contain suitable nitrogen sources and will be supplemented where necessary with lactose as the only carbon source or as the major carbon source.

After practical completion of cell growth has been completed (i.e. growth to a point such that further cell growth and/or further lactase production is uneconomical), the mycelium will be harvested. The cell harvesting and lactase recovery procedure may be carried out by known procedures which are sufficiently drastic to free the lactase from the cell structures and causing it to pass into a liquid aqueous phase. However, we have found that it is not necessary to use such drastic separation procedures and that milder procedures may be employed which leave the lactase attached in some manner to the ruptured cells. Illustrative examples are given below. In any event the mycelium is separated from the spent broth or culture medium; it is broken down mechanically to the desired degree and large particles of mycelium are removed. Well known separation techniques such as filtration, centrifugation, precipitation with polyacrylic acid, column chromatography using carboxymethyl cellulose, gel exclusion chromatography using various Sephadex products, etc. may be used to separate and concentrate the lactase fraction or component of the mycelium. It is not necessary to produce a pure enzyme.

The enzyme may be used in solution or it may be immobilized on suitable support materials such as porous glass beads, activated agarose, comminuted hide collagen, etc. Methods of bonding the enzyme to solid materials include covalent bonding (see Zaborsky, Immobilized Enzymes, CRC Press (1973)) and hydrophobic bonding (see Hofstee, Biochemical and Biophysical Research Communications, 53, 1137 – 1144 (1973)).

The lactase of the present invention has a high degree of activity and it retains its activity at temperatures of 60° C. or higher. This enables it to be used efficiently in industrial processing of dairy products at elevated temperatures. Among its advantages are the following: At such temperatures the hydrolysis of lactose proceeds more rapidly than at lower temperatures. The enzyme may be put to use in industrial processes at or close to high temperatures which prevail in the process; that is to say, the introduction of lactose hydrolysis into the process does not require substantial modification of or the introduction of a separate step into a conventional process. Further, where the hydrolysis step is carried out at 60° C. or higher, the growth of unwanted organisms such as bacterial or fungal species that commonly induce spoilage of the product are inhibited. A further advantage of the lactase of the present invention arises from the fact that much if not all of this lactase exhibits maximum activity at a low pH, e.g. between 4 and 5. Certain fermentation processes such as the production of buttermilk, yogurt and sour cream proceed at low (acid) pH. The lactase of the present invention can be used to advantage in such processes. Further, a mixture of (1) conventional lactase, e.g. from K. fragilis (which has its optimum activity at about pH 7) with (2) lactase of the present invention may be used to advantage, e.g. mixtures of 20 to 80 parts by weight of lactase of the present invention and 80 to 20 parts by weight of conventional lactase. This mixture of enzymes may be added at a point in the process where the temperature is low (e.g. 40° C.) and/or the pH is high (e.g. close to 7) at which point the conventional lactase is most effective. Then during a subsequent phase of the process where the temperature is higher (e.g. 50° – 60° C. or higher) and/or the pH is low (e.g. 4 to 5), the lactase of the present invention is most effective.

In FIG. 1, which is a composite diagram of several dairy product processes, several uses of the lactase of the present invention are shown.

Referring now to FIG. 1, raw milk enters the system at 10 and typically may contain about 3½ percent butterfat and 8.6 percent of solids non-fat. The milk passes to a storage unit where it is held at a suitable low temperature, for example less than 40° F. (4.4° C.). The raw milk passes out of storage through line 12 and may be warmed if desired in a heating unit (not shown) to, for example 100° F. It then passes to a centrifuge 13 for separation, clarification and/or standardization. Double headed arrows 14 and 15 indicate that in this step butterfat may be removed or may be added and non-fat milk solids may be removed and/or added. The milk then passes through line 16 to the next stage of the process. At this point in accordance with one embodiment of the present invention, the lactase of the present invention is added through line 17, for example in an amount equal to about 0.03 percent of the weight of raw milk. (Proportionately more will be added to a concentrated milk product.) The lactase may be solely that produced in accordance with the invention or it may be a mixture of yeast lactase and lactase of the present invention as described above. The milk may then pass through line 18 to a storage unit 19 where it is held at a low temperature, for example below 40° F. and then passes out as needed through line 20. Alternatively, the milk may pass directly through line 21.

Figure 6:
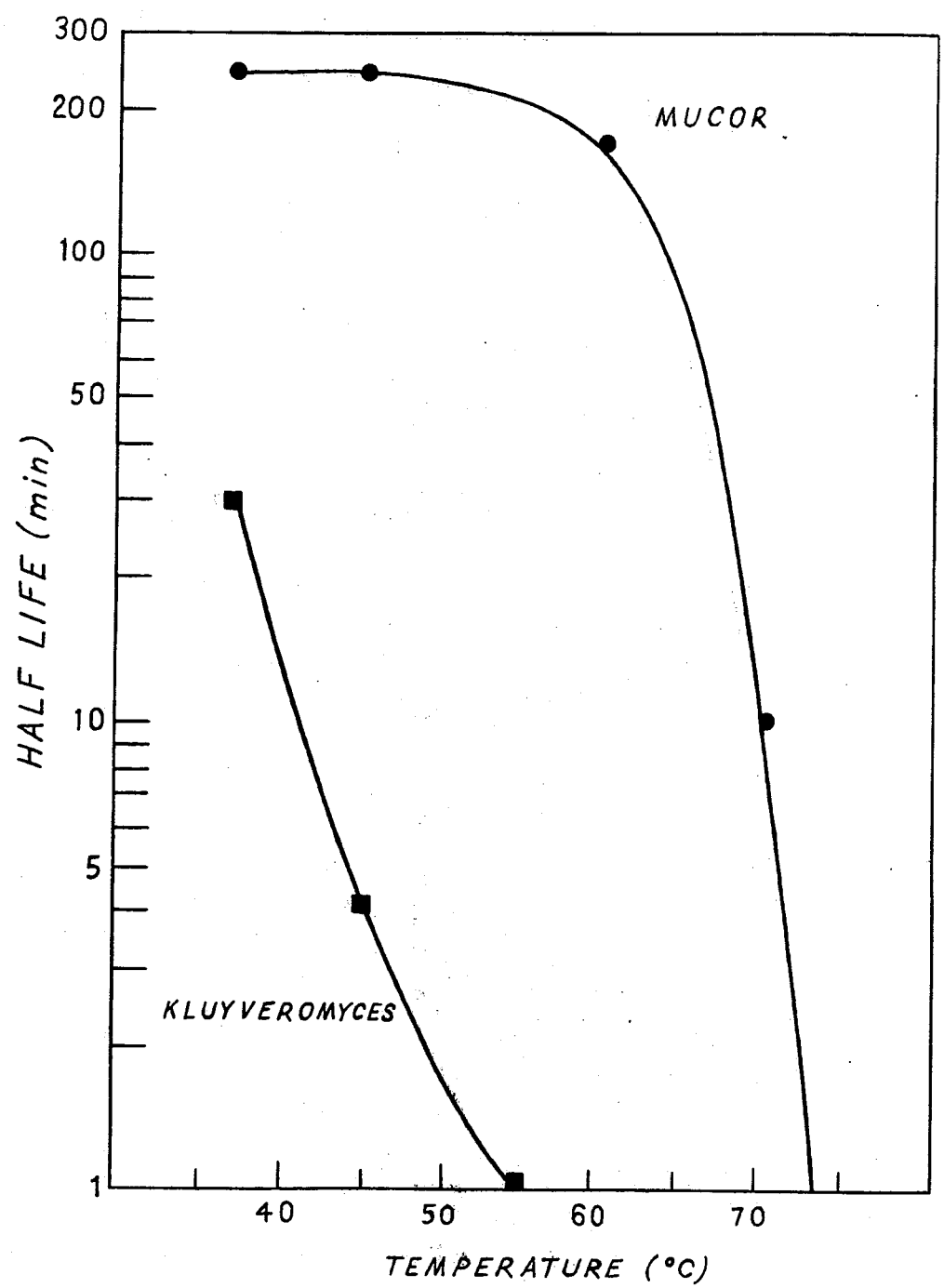

In either case the milk passes by way of line 25 through a heat regeneration unit or heat exchanger 26 which serves the purpose of preheating the incoming milk in part by heat exchange with outgoing treated milk that has been heated in a subsequent stage of the process. If desired during its passage through the heat exchanger, the milk may be subjected to a homogenizing step (not shown). In one embodiment milk passes out of the heat exchanger through line 27 to a preheating unit 28 wherein it is heated, typically to a temperature of 140° F., and then passes out through line 29 to a holding unit 30. In the high temperature short time (HTST) procedure most often employed in the dairy products industry, the temperature in unit 30 will be typically about 161° F. and the holding time 15 seconds. This accomplishes pasteurization. The preheating unit 28 is used to raise the temperature close to that in the next unit and at the temperature prevailing in unit 28 the lactase is stable and accomplishes hydrolysis of lactose. The lastase of the present invention is thermostable in comparison to conventional lactase such as that derived from yeast nevertheless at 161° F. (approximately 71.7° C.) it loses activity more rapidly than at 140° F. However, the lactase of the present invention, as shown by FIG. 6, retains a high degree of activity for a considerable period of time even at 70° C. It may be assumed that hydrolysis of lactose occurs in units 26, 28 and 30.

The pasteurized product passes out of unit 30 through line 31 to a vacuum pan dehydration unit 32. Assuming that condensed milk is the end product, this dehydration will be partial only and the partially evaporated or condensed milk passes out of the unit 32 through line 33 to a filler 34 wherein it is filled into containers which are closed by an appropriate closing unit. The end product passes out through line 35. Under the conditions described and illustrated, most or all of the lactose will have been hydrolyzed to glucose and galactose.

Alternatively, the concentrated product may pass out of the vacuum unit 32 through line 40 to a spray drier 41 wherein it is spray dried at for example 220° F. or 300° to 400° F. The dry milk powder is removed through line 42 and suitably packaged.

Another branch of the process is illustrated by line 43 through which the partially evaporated product passes and sucrose is introduced through line 43a to sweeten the product which then passes into a filler 44 wherein the product is filled into cans which are closed by a suitable closing machine. The canned product leaves through line 45 and constitutes the end product, which in this case is sweetened condensed milk.

Another branch of the process is shown in which the product leaves the pasteurization unit 30 through line 46 and passes down through the heat exchanger 26 giving up its heat to incoming cold milk by heat exchange. If a fermented product such as buttermilk, sour cream or yogurt is the end product of the process, the pasteurized milk passes from the heat exchanger through line 47. Homogenization may occur at this point. The lactase of the present invention (either alone or in admixture with conventional lactase produced from yeast as described above) is introduced through line 48. The pasteurized milk containing the added enzyme may then pass through line 49 to suitable fermentation equipment (not shown) to produce buttermilk, or it may pass through line 50 to suitable equipment (not shown) to produce sour cream, or it may pass through line 55 to yogurt vats 56 wherein it is held at 105° to 110° F. (40.6° – 43.3° C.). During these processes, if a lactase mixture is employed, the thermolabile lactase (e.g. yeast lactase) will be effective at the lower temperature — high (neutral) pH phase of fermentation and the lactase of the present invention takes over as the temperature increases and the pH diminishes. In yogurt production, the semi-processed product leaves vats 56 through line 57 and is inoculated with suitable bacteria introduced through line 58. The inoculated product may then pass through a line 59 to fermenting equipment 60. The product passes out through line 61. Flavor and color are added through line 62 and the product is then packaged. Alternative branch 63 bypasses the fermentation equipment. Fruit may be introduced at 64.

If the end product is to be whole fresh milk, the pasteurized whole milk leaves heat exchanger 26 through line 70 to storage 71 then through line 72 to a packaging operation. Alternatively the pasteurized milk may pass directly by line 73 to a packaging operation.

In another application of the invention whey is treated. Whey is a waste product in the manufacture of cheese and its disposition is a severe problem. It may be treated with the lactase of the present invention and held at a temperature of about 60° C. for a time sufficient to convert the lactose to glucose and galactose and may then be used as a food ingredient for human or animal consumption.

An added advantage of the invention is that by hydrolyzing the lactose content of whole milk, whey or other dairy products to glucose and galactose, a sweeter product having no greater calory content is produced. Yet, another advantage is that by removal of lactose its tendency to crystallize in the manufacture of ice cream and other concentrated milk products is eliminated.

The term "thermophilic fungi" is used herein to mean fungi which exhibit optimum growth at about 40° to 50° C.

The following specific examples will serve further to illustrate the practice and advantages of the invention. Cultures, chemicals, method of screening and method of assay were as follows:

Cultures

All cultures were maintained on YpSs agar (Cooney and Emerson, "Thermophilic fungi", etc., W. H. Freeman & Co., San Francisco, 1964) and exhibited an optimum growth temperature at or above 40° C. Spore suspensions used as inocula for submerged cultures were prepared from YpSs agar bottle cultures after 3 days at 45° C. Lilly and Barnett's basal medium (1951) containing 0.9% lactose as a sole carbon source was used on a shaker apparatus for 3 days at 45° C. to obtain sufficient mycelium for screening and assay studies. Freeze-dried cells of *Kluyveromyces* (*Saccharomyces*) *fragilis* 55–61, derived from NRRL Y-1109, were obtained from the Yeast Culture Collection, Dept. of Food Science & Technology, University of California, Davis and were used directly. These yeast cells had been propagated in a nutrient broth containing 10% lactose, 0.5% 5N $NH_4OH$, 0.5% yeast extract and 0.3% $KH_2PO_4$ at pH 4.4 and 30° C.

Chemicals

Glucostat reagent, used for glucose determinations after hydrolysis of lactose, was obtained from Worthington Biochemicals Corp. (Freehold, N.J.) and was prepared according to label directions. Chemicals were of reagent grade and distilled water was used in all procedures except for preparing culture media. A substrate containing 5% lactose was used for all assays and buffers were prepared at an ionic strength of 0.1M. A Beckman Model DB-1401 spectrophotometer was used for colorimetric measurements at a wavelength of 420 nm.

Screening

Preliminary tests for the production of lactase were based on fungus growth occurring on plates of the basal medium with lactose as the sole carbon source. [Attempts to induce Lactose production were unsuccessful; see J. Food Science 39, No. 6, page 1184 (1974).] Sufficient quantities of mycelium from lactase-positive cultures were obtained from shake cultures in the lactose-containing basal medium (broth) after 24 – 96 hr. at 45° C. The mycelium was harvested by filtering and washing with distilled water, the used immediately or freeze dried for later analysis.

Assays

The enzymatic activity of each culture was measured by the Glucostat reaction, a glucose oxidase, peroxidasechromogen determination of the glucose formed from lactose hydrolysis, as modified from the method used by Dahlquist (1964). Enzyme extracts were prepared from freeze-dried fungal cells suspended in postassium phosphate buffer (pH 6.6) by grinding in a mortar with a minimal amount of sand. The extract was suspended in 10 ml of buffer containing 5% lactose at 37° C. The hydrolytic reaction was terminated after 1 hr. by boiling for 10 min. Cell fragments and residual sand was removed by centrifugation at 4,600 × G for 5 min. and the Glucostat reaction was performed on a 2-ml aliquot of the centrifugate. A duplicate sample of the enzyme preparation, denatured by boiling for 15 min. before the lactose hydrolysis, was used as a spectrophotometric reagent blank. Both freeze-dried and fresh mycelial cell extracts were assayed to determine the effect of freeze drying on observed lactase activity.

Enzymatic Activity

This was measured as $\mu$moles (micro moles) of lactose hydrolyzed per milligram of cells (dry weight) of harvested mycelium (processed as described above) after 1 hour at pH 6.6 and 37° C.

Optimum pH and Temperature

Only those cultures which showed the best cell yield and enzymatic activity were tested. They were assayed again using buffers of different pH values in a range varied between pH 3.8 and 6.6 in 0.2 increments. Because of its extended buffering capacity at lower pH values, sodium citrate buffer was used in these pH studies rather than the postassium phosphate buffer used in the initial assays. At the determined optimum of pH 4.4, the optimum temperature for enzymatic activity was determined by conducting the hydrolysis at various temperatures between 25° and 70° C.

Thermostability Determination

This was determined and compared to that of a similar preparation from the yeast *K. fragilis*. Fresh mycelium was ground in citrate buffer (pH 4.4) and diluted to a suspended concentration of 44 mg/ml (dry wt). Freeze-dried yeast cells were suspended in phosphate buffer (pH 6.6), 2% toluene was added to disrupt the cells, and the suspension was allowed to stand for 6 hr. before being brought to a final concentration of 0.2 mg/ml (dry wt). Triplicate sets of tubes, each containing 4 ml of the yeast or fungus preparation, were incubated in water baths at 37°, 45°, 60° and 70° C. for periods ranging from 1 min. to 2 hr. After incubation, the tubes were cooled in an ice bath and the extent of denaturation was measured by the observed loss of enzymatic activity under the optimum conditions of temperature and pH for each preparation.

Results

Cultures of 54 strains of thermophilic filamentous fungi, representing over 15 species of 12 genera, were tested for their ability to produce lactase. All strains were capable of exhibiting some growth at 45° C. on a culture medium containing lactose as a sole carbon source. 25 strains exhibiting the best growth on the lactose medium were recultured in shaker culture. Enzymatic activities for selected strains from the genera Chaetomium, Humicola, Malbranchea, Mucor, Sporotricum and Torula are shown in Table 1. Freeze-dried preparations from the mycelium of the fungi tested hydrolyzed between 0.03 to 0.95 $\mu$moles lactose/mg (dry wt) of cells after 1 hr. at pH 6.6 and 37° C. Mycelial dry weight was determined after oven drying at 70° C. for 36 hr.

Figure 2:
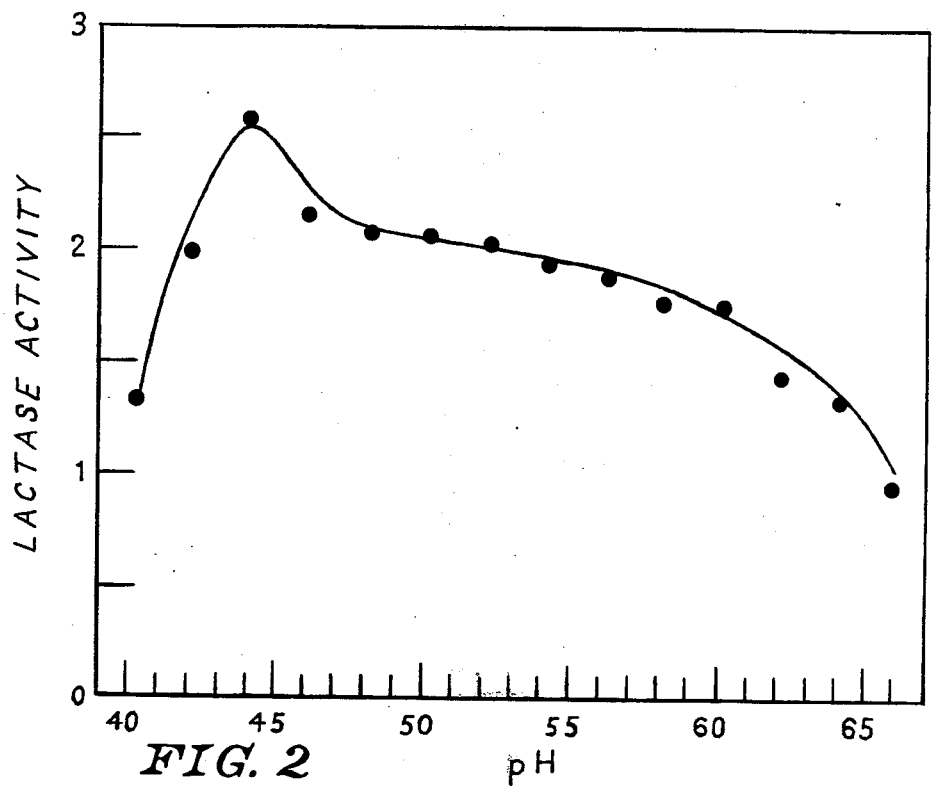
Figure 3:
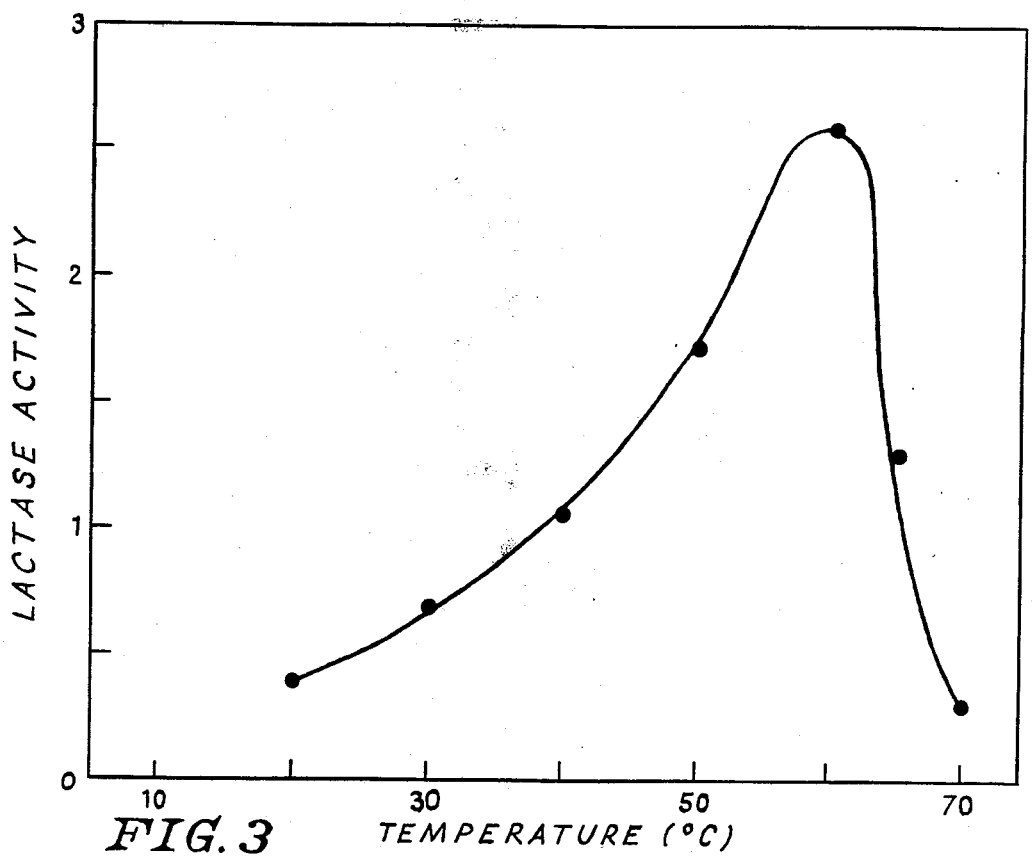

Four strains of *Mucor pusillus* exhibited the greatest enzymatic activity, 0.81 – 0.95 $\mu$mole/mg, and were studied to determine the pH and temperature optima of their thermophilic lactase. At the optimum pH of 4.4 these strains exhibited activities of 1.15 – 1.36 $\mu$mole/mg that were 45% greater than those at pH 6.6 (FIG. 2). The Mucor enzyme preparations exhibited a broader range of activity with respect to pH, with more than 75% of the maximum activity being maintained through a range of pH 4.1 – 5.5. At pH 4.4, the greatest catalytic activity, 1.58 – 2.58 μmole/mg, occurred when lactose hydrolysis was carried out at 61° C. and at least 75% of the maximum activity was retained between 53° and 63° C. (FIG. 3). Preparations from fresh mycelium were more active than preparations from freeze-dried cells and hydrolyzed 4.15 – 7.21 μmole of lactose/mg and 1.56 – 2.61 μmole/mg, respectively. By using the optimum pH and temperature determined here, the enzymatic activities of crude preparations from fresh mycelium were 4 – 6.7 times higher than those observed during the preliminary assays conducted at pH 6.6 and 37° C. using preparations from freeze-dried cells.

Figure 4:
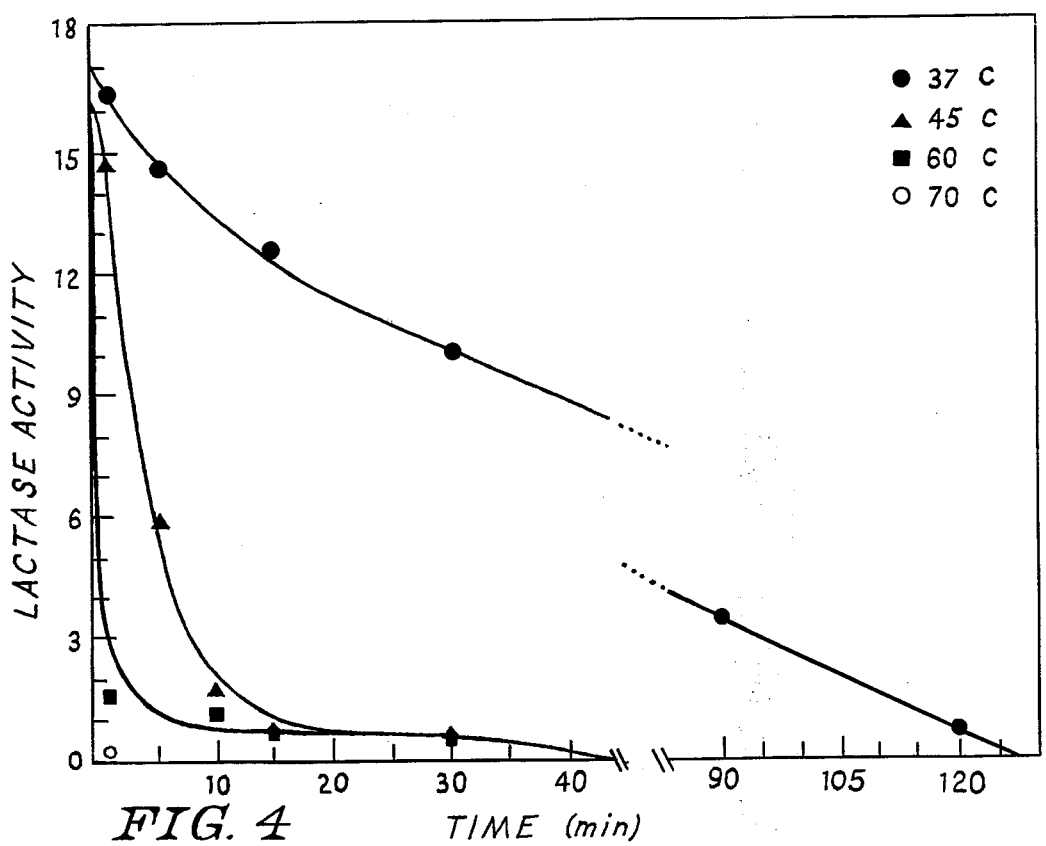
Figure 5:
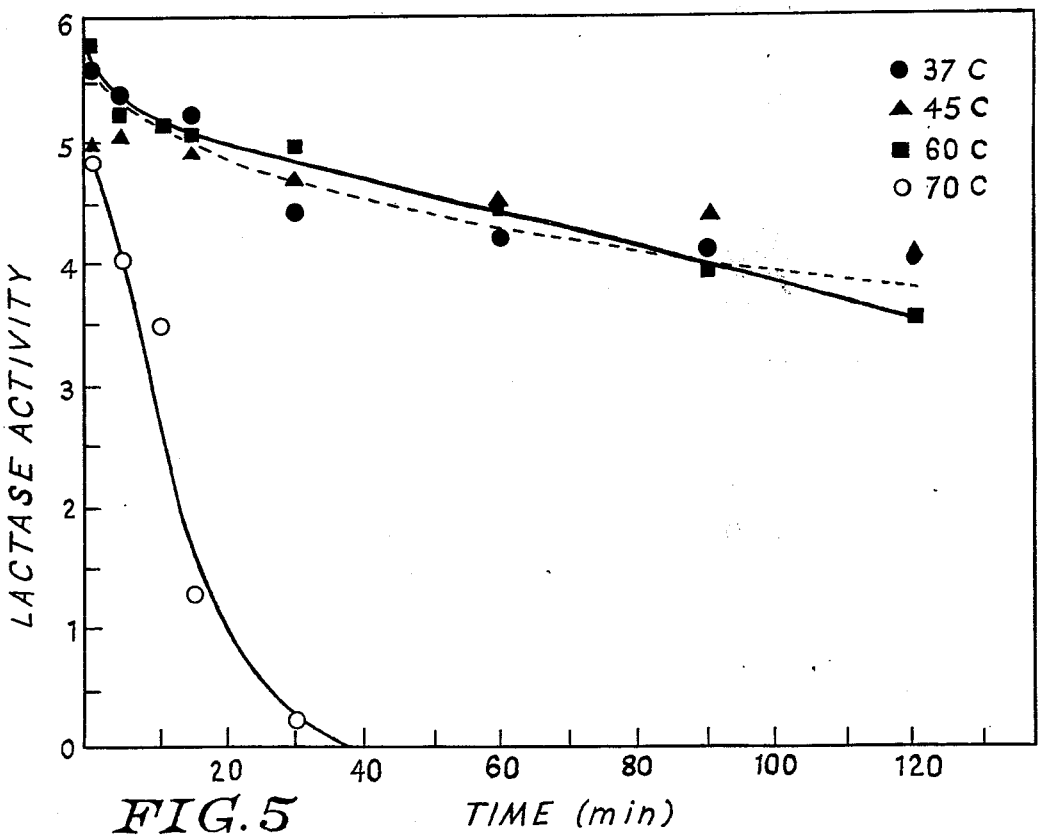

A comparison of the thermostability of the *M. pusillus* (3 – 4 – 1) enzyme with that of *K. fragilis* showed that although the yeast produced approximately three times more activity per hour, 96% of this activity was lost within 10 min. at 60° C. (FIG. 4). The thermostable Mucor enzyme lost only 27% of its activity after 1 hr. at 60° C. and retained more than 60% of its activity after 2 hr. at this temperature (FIG. 5). This difference in thermostability can also be noted in terms of the half-life of enzymatic activity (FIG. 6). The yeast enzyme had a half-life of less than 1 min. at 60° C. while the thermophile enzyme had a half-life of 180 min. at this temperature. The thermostability of the Mucor enzyme was significantly greater at other temperatures as well.

and a temperature of 35° C of lactase derived from *K. fragilis* NRRL Y-1109.

3. The lactase of claim 1 derived from the genus Mucor.

4. The lactase of claim 1 derived from *Mucor pusillus*.

5. The lactase of claim 1 derived from the genus Sporotrichum.

6. The lactase of claim 1 derived from *Torula thermophila*.

7. The lactase of claim 1 wherein the lactase is attached to cell remnants of the fungal mycelium.

8. Lactase that is thermostable and that has optimum activity at a pH not greater than 5.

9. An admixture of (1) thermostable lactase and (2) thermolabile lactase, said lactase (1) having and retaining a high degree of enzymatic activity at a temperature of 55° – 60° C. and a pH between 4 and 5, said lactase (2) having its optimum activity and stability at temperatures substantially below 55° C. and at a pH about 7; each said lactase component being present in substantial proportion sufficient to effectively catalyze hydrolysis of lactose to glucose and galactose at its optimum conditions of temperature and pH.

10. A method of producing thermostable lactase having its optimum activity at a pH below 5 which comprises inoculating a culture medium having lactose as the sole or a major source of carbon with cells of a thermophilic fungus, said culture medium being suitable for proliferation of such cells, maintaining conditions of temperature and pH favorable to cell growth Table 1

| Lactase Activity of Thermophilic Filamentous Fungi Strains | | | |
|---|---|---|---|
| Organism | Screened | Assayed | Activity |
| Aspergillus sp. | 2 | * | |
| Chaetomium sp. | 3 | | |
| C. thermophile var. coprophile | 3 | 1 | 0.12 |
| Humicola grisea var. thermoidea | 2 | 2 | 0.03–0.12 |
| H. isolens | | | |
| H. lanuginosa | 2 | 1 | 0.03 |
| Malbranchea pulchella var. sulfurea | 3 | 2 | 0.07–0.14 |
| Mucor miehei | 3 | 2 | 0.15–0.29 |
| M. pusillus | 15 | 11 | 0.13–0.95 |
| Mucor sp. | 7 | 2 | 0.28–0.89 |
| Myriococcum albomyces | 1 | | |
| Papulospora thermophila | 2 | | |
| Penicillium sp. | 1 | | |
| Rhizopus sp. | 1 | | |
| Sporotrichum sp. | 1 | 1 | 0.65 |
| S. thermophile | 2 | 2 | 0.18–0.33 |
| Thermoascus aurantiacus | 2 | | |
| Torula sp. | 1 | | |
| T. thermophila | 1 | 1 | 0.58 |

*Only strains exhibiting good growth on lactose-containing media were assayed quantitatively.

It will therefore be apparent that a new and useful enzyme preparation and methods of production of such enzyme have been provided and new and useful methods of hydrolyzing lactose to glucose and galactose have been provided.

We claim:

1. Lactase derived from thermophilic fungi and in a form suitable for use in catalyzing the hydrolysis of lactose in a dairy product to glucose and galactose, said lactase having a high enzymatic activity and being characterized by retention of such activity for a substantial period of time at a temperature of 55° – 60° C and a pH not exceeding 5.

2. The lactase of claim 1 having an activity at a pH not exceeding 5 and at a temperature of 60° C which is not substantially less than the activity at a neutral pH and proliferation, causing such growth and proliferation, and harvesting the resulting mycelium, said fungus being selected from a genus and species capable of producing thermostable lactase in such culture medium at a substantial rate, such lactase having its maximum activity at a pH below 5.

11. The method of claim 10 wherein the fungus is a filamentous thermophile.

12. The method of claim 10 wherein the fungus is of the genus Mucor.

13. The method of claim 10 wherein the fungus is *Mucor pusillus*.

14. The method of claim 10 wherein the fungus is of the genus Sporotrichum.

15. The method of claim 10 wherein the fungus is *Torula thermophila*.

16. A method of treating a dairy product to reduce its lactose content by hydrolyzing the lactose to glucose and galactose; said method comprising subjecting the dairy product to contact with thermostable lactase having its optimum activity at a pH not greater than 5, said contact being at a temperature not less than about 55° C and at a pH not greater than 5 and causing hydrolysis of lactose at such temperature.

17. The method of claim 16 wherein the lactase is derived from thermophilic fungi.

18. The method of claim 16 wherein the lactase is derived from filamentous thermophilic fungi.

19. The method of claim 16 wherein the lactase is derived from *Mucor pusillus*.

20. The method of claim 16 wherein the lactase is derived from the genus Sporotrichum.

21. The method of claim 16 wherein the lactase is derived from *Torula thermophila*.

* * * * *